US00PP19333P2

(12) United States Plant Patent
Heuger

(10) Patent No.: US PP19,333 P2
(45) Date of Patent: Oct. 14, 2008

(54) ***ARGYRANTHEMUM* PLANT NAMED 'SUN 10'**

(50) Latin Name: *Argyranthemum frutescens*
Varietal Denomination: Sun 10

(76) Inventor: Josef Heuger, Postfach 11 03, D-49215 Glandorf (DE)

( * ) Notice: Subject to any disclaimer, the term of this patent is extended or adjusted under 35 U.S.C. 154(b) by 0 days.

(21) Appl. No.: 11/903,798

(22) Filed: Sep. 25, 2007

(51) Int. Cl.
*A01H 5/00* (2006.01)

(52) U.S. Cl. ..... Plt./406; Plt./263
(58) Field of Classification Search ..... Plt./406, Plt./263
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Argyranthemum* plant named 'Sun 10', characterized by its compact and uniform plant habit; freely branching growth habit; freely flowering habit; single type inflorescences with white-colored ray florets; and good garden performance.

2 Drawing Sheets

Botanical designation: *Argyranthemum frutescens.*
Cultivar denomination: 'Sun 10'.

BACKGROUND OF THE INVENTION

The present invention relates to a new and distinct cultivar of *Argyranthemum* plant, botanically known as *Argyranthemum frutescens* and hereinafter referred to by the name 'Sun 10'.

The objective of the breeding program is to create new compact *Argyranthemum* cultivars with attractive ray and disc floret colors and good garden performance.

The new *Argyranthemum* originated from a cross-pollination made by the Inventor in July, 2004 in Glandorf, Germany of two unnamed seedling selections of *Argyranthemum frutescens,* not patented. The new *Argyranthemum* was discovered and selected by the Inventor as a single flowering plant within the progeny of the stated cross-pollination in a controlled environment in Glandorf, Germany in July, 2005.

Asexual reproduction of the new *Argyranthemum* by vegetative tip cuttings was first conducted in Glandorf, Germany in February, 2006. Asexual reproduction by cuttings has shown that the unique features of this new *Argyranthemum* are stable and reproduced true to type in successive generations.

SUMMARY OF THE INVENTION

Plants of the cultivar Sun 10 have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sun 10'. These characteristics in combination distinguish 'Sun 10' as a new and distinct potted *Argyranthemum* cultivar:

1. Compact and uniform plant habit.
2. Freely branching growth habit.
3. Freely flowering habit.

4. Single type inflorescences with white-colored ray florets.
5. Good garden performance.

Plants of the new *Argyranthemum* differ from plants of the parent selections primarily in plant size and uniformity.

Plants of the new *Argyranthemum* can be compared to plants of the *Argyranthemum* cultivar Dana, not patented. In side-by-side comparisons conducted in Glandorf, Germany, plants of the new *Argyranthemum* differed from plants of the cultivar Dana in the following characteristics:

1. Plants of the new *Argyranthemum* had darker green-colored leaves than plants of the cultivar Dana.
2. Plants of the new *Argyranthemum* had larger inflorescences than plants of the cultivar Dana.
3. Inflorescences of plants of the new *Argyranthemum* had more ray florets than inflorescences of plants of the cultivar Dana.

BRIEF DESCRIPTION OF THE PHOTOGRAPHS

The accompanying photographs illustrate the overall appearance of the new *Argyranthemum.* These photographs show the colors as true as it is reasonably possible to obtain in colored reproductions of this type. Colors in the photographs may differ slightly from the color values cited in the detailed botanical description which accurately describe the colors of the new *Argyranthemum.*

The photograph on the first sheet comprises a side perspective view of a typical flowering plant of 'Sun 10' grown in a container.

The photograph at the top of the second sheet is a close-up view of typical inflorescences of 'Sun 10'.

The photograph at the bottom of the second sheet is a close-up view of a typical leaf of 'Sun 10'.

DETAILED BOTANICAL DESCRIPTION

The aforementioned photographs and following observations and measurements describe plants grown during the spring in Glandorf, Germany in a glass-covered greenhouse and under conditions and practices which approximate those generally used in commercial potted *Argyranthemum* production. During the production of the plants, day temperatures ranged from 14° C. to 28° C., night temperatures ranged from 10° C. to 18° C. and light levels ranged from 25,000 lux to 90,000 lux. Plants were pinched one time. Plants used in the photographs and for the description were about eleven weeks old. In the following description, color references are made to The Royal Horticultural Society Colour Chart, 2001 Edition, except where general terms of ordinary dictionary significance are used.

Botanical classification: *Argyranthemum frutescens* cultivar Sun 10.

Parentage:

*Female, or seed, parent.*—Unnamed seedling selection of *Argyranthemum frutescens,* not patented.

*Male, or pollen, parent.*—Unnamed seedling selection of *Argyranthemum frutescens,* not patented.

Propagation:

*Type.*—Terminal cuttings.

*Time to initiate roots, summer.*—About 8 to 10 days at temperatures of about 18° C. to 24° C.

*Time to initiate roots, winter.*—About 10 to 15 days at temperatures of about 14° C. to 18° C.

*Time to produce a rooted young plant, summer.*—About 14 to 16 days at temperatures of about 18° C. to 24° C.

*Time to produce a rooted young plant, winter.*—About 16 to 20 days at temperatures of about 14° C. to 18° C.

*Root description.*—Fine to medium in thickness, fibrous; white in color.

*Rooting habit.*—Moderately dense.

Plant description:

*Appearance.*—Herbaceous single type potted *Argyranthemum.* Compact and uniform plant habit. Strong and freely branching growth habit with about four lateral branches developing per plant; dense and full plants. Low to moderately vigorous growth habit.

*Plant height.*—About 14.6 cm.

*Plant width.*—About 22.7 cm.

*Lateral branches.*—Length: About 5.6 cm. Diameter: About 3 mm. Internode length: About 6 mm. Strength: Strong; young stems, flexible. Texture: Smooth, glabrous. Color: 144A to 144B.

Foliage description:

*Arrangement.*—Alternate, simple; sessile.

*Length.*—About 7.1 cm.

*Width.*—About 3.6 cm.

*Shape.*—Pinnatisect.

*Apex.*—Acute.

*Base.*—Broadly cuneate.

*Margin.*—Pinnatifid; laciniate.

*Texture, upper and lower surfaces.*—Smooth, glabrous.

*Venation.*—Pinnate.

*Color.*—Developing foliage, upper surface: 137A to 137B. Developing foliage, lower surface: 138A. Fully expanded foliage, upper surface: 137A; venation, 143A. Fully expanded foliage, lower surface: 138A; venation, 143A to 143B.

Inflorescence description:

*Appearance.*—Single type inflorescence form with obovate-shaped ray florets. Inflorescences borne on terminals above foliage. Disc and ray florets arranged acropetally on a capitulum. Inflorescences moderately fragrant, pleasant.

*Flowering season.*—Plants flower from spring to late summer in Germany; flowering continuous during this period.

*Inflorescence longevity.*—Inflorescences last about two weeks on the plant; inflorescences not persistent.

*Quantity of inflorescences.*—Freely flowering habit, about eleven inflorescences develop per lateral branch.

*Inflorescence bud.*—Height: About 9 mm. Diameter: About 9 mm. Shape: Globular. Color: N138B; towards the apex, 145C to 145D.

*Inflorescence size.*—Diameter: About 4.1 cm. Depth (height): About 1.5 cm. Diameter of disc: About 5 mm. Receptacle diameter: About 9 mm. Receptacle height: About 3 mm.

*Ray florets.*—Shape: Obovate. Length: About 1.9 cm. Width: About 8 mm. Apex: Emarginate, praemorse. Base: Cuneate. Margin: Entire. Texture, upper and lower surfaces: Smooth, glabrous. Number of ray florets per inflorescence: About 39 in about three whorls. Color: When opening, upper and lower surfaces: Close to 155D. Fully opened, upper and lower surfaces: Close to 155D.

*Disc florets.*—Arrangement: Massed at center of receptacle. Shape: Tubular, elongated. Apex: Five-pointed. Length: About 6 mm. Diameter, apex: About 2 mm. Diameter, base: About 0.8 mm. Number of disc florets per inflorescence: About 100. Color, immature: Towards the apex, 13A to 13B; towards the base, 145C to 145D. Color, mature: Towards the apex, 13B; mid-section, 145C; towards the base, 145D.

*Phyllaries.*—Number of phyllaries per inflorescence: About 20 arranged in two whorls. Length: About 5.5 mm. Width: About 3 mm. Shape: Obovate. Apex: Rounded. Base: Cuneate. Margin: Entire. Texture, upper and lower surfaces: Smooth, glabrous; margins, papery. Color, upper surface: 146B. Color, lower surface: 143A.

*Peduncles.*—Length: About 5.5 cm to 6.2 cm. Diameter: About 1.5 cm. Angle: Mostly erect to about 25° from vertical. Strength: Strong, flexible. Texture: Smooth, glabrous. Color: 138A.

*Reproductive organs.*—Androecium: Present on disc florets only. Anther length: About 2 mm. Anther shape: Lanceolate. Anther color: 14B. Pollen amount: Scarce. Pollen color: 14A. Gynoecium: Present on both ray and disc florets. Pistil length: About 2 mm. Stigma shape: Two-parted. Stigma color: 14B. Style length: About 1 mm. Style color: 154D. Ovary color: 150C to 150D.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 0° C. to about 40° C.

It is claimed:

1. A new and distinct *Argyranthemum* plant named 'Sun 10' as illustrated and described.

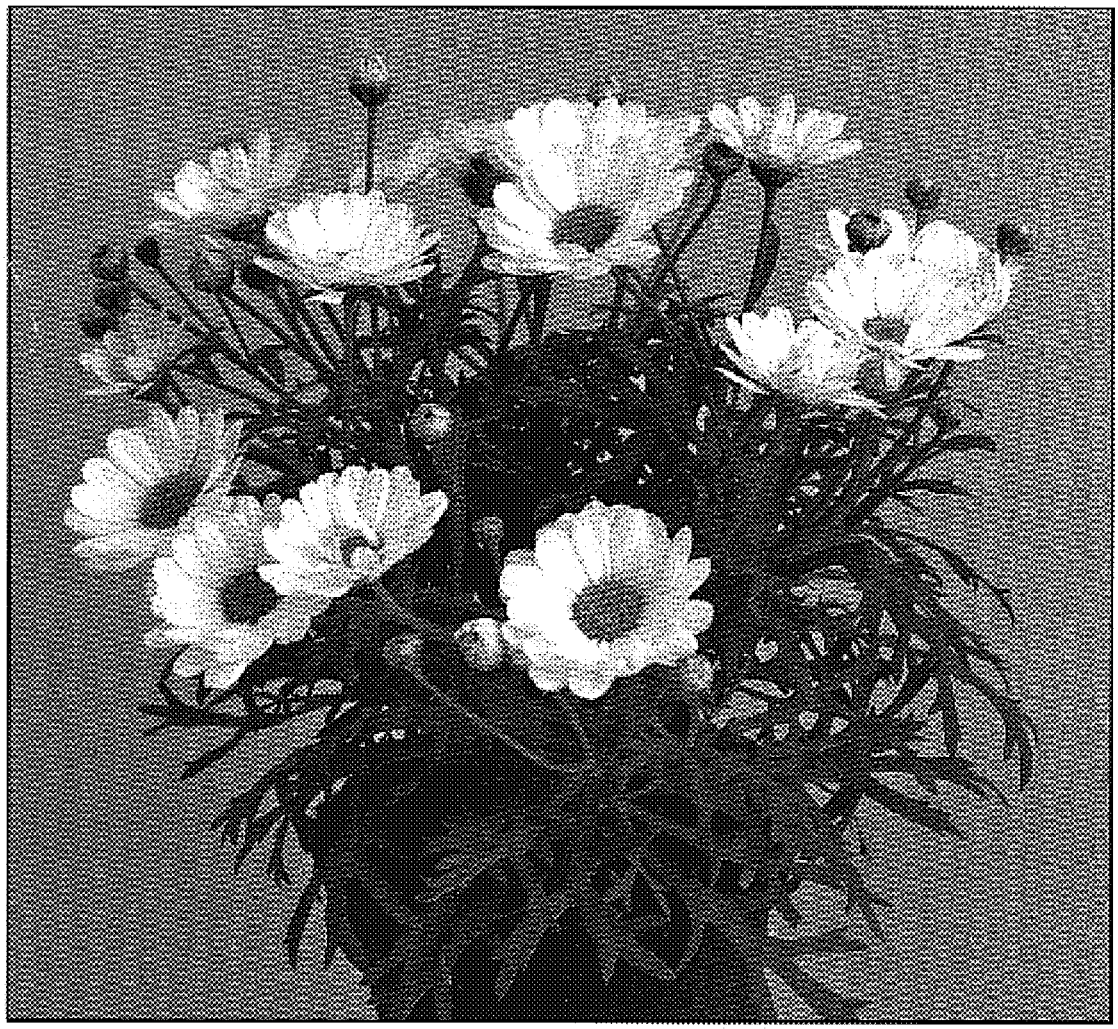

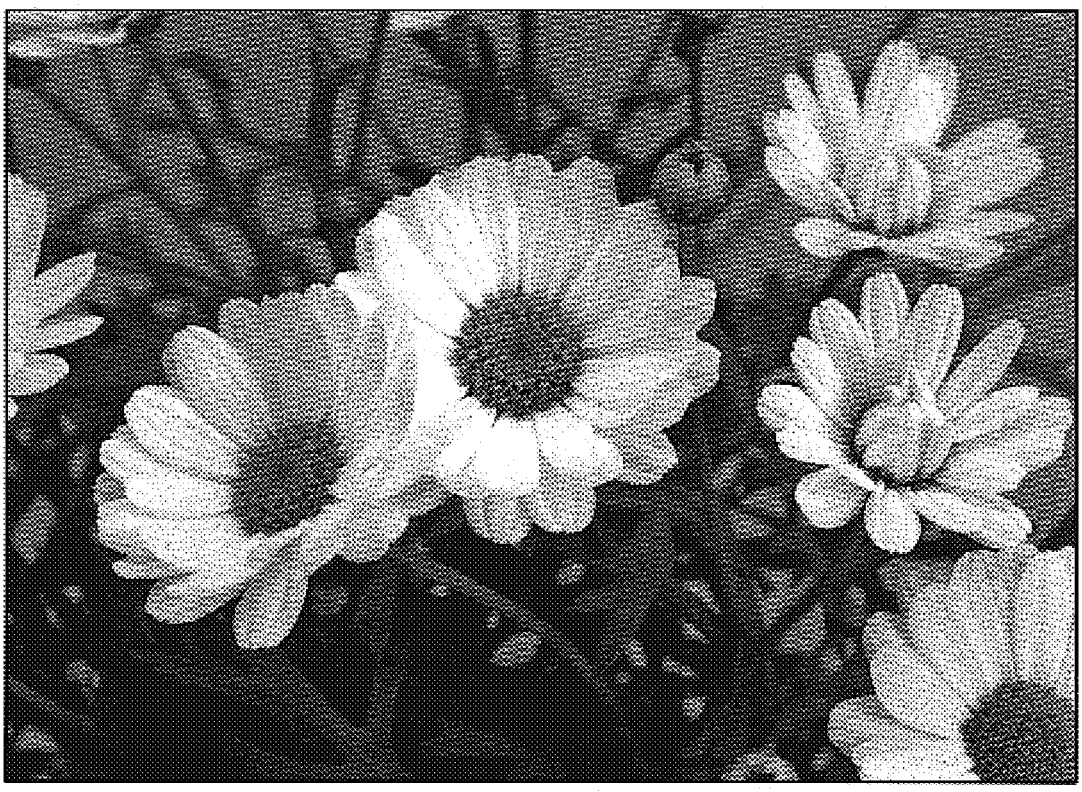
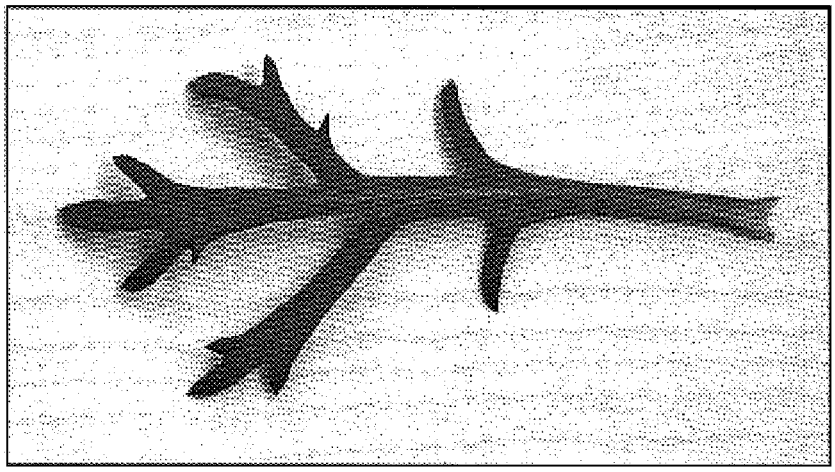

* * * * *